United States Patent [19]

Umeda et al.

[11] Patent Number: 5,000,030

[45] Date of Patent: Mar. 19, 1991

[54] METHOD AND APPARATUS FOR MEASURING DYNAMIC RESPONSE CHARACTERISTICS OF SHOCK ACCELEROMETER

[75] Inventors: Akira Umeda; Kazunaga Ueda, both of Tsukuba, Japan

[73] Assignees: Agency of Industrial Science & Technology; Ministry of International Trade & Industry, Tokyo, Japan

[21] Appl. No.: 494,396

[22] Filed: Mar. 16, 1990

[30] Foreign Application Priority Data

Aug. 4, 1989 [JP] Japan ............................ 1-203501

[51] Int. Cl.⁵ ............................................ G01P 21/02
[52] U.S. Cl. .................................................. 73/1 D
[58] Field of Search ............... 73/1 D, 1 DV, 1 DC, 73/2, 12

[56] References Cited

U.S. PATENT DOCUMENTS 3,830,091 8/1974 Sinsky ........................ 73/1 DV

FOREIGN PATENT DOCUMENTS 0492817 2/1976 U.S.S.R. ............................ 73/1 D
0993131 1/1983 U.S.S.R. ............................ 73/1 D
1191833 11/1985 U.S.S.R. ............................ 73/2

Primary Examiner—Robert R. Raevis
Attorney, Agent, or Firm—Oblon, Spivak, McClelland, Maier & Neustadt

[57] ABSTRACT

A method for measuring the dynamic response characteristics of an shock accelerometer comprises the steps of attaching an accelerometer to be tested and a strain gage to one end of a rod supported to be axially slidable, imparting an impact to the other end of the rod, inputting the acceleration arising when the elastic wave reflect from the end surface of the rod to the accelerometer and the strain gage, subjecting the outputs of the accelerometer and the strain gage to data processing and error compensation to obtain the gain and phase characteristics of the accelerometer.

10 Claims, 12 Drawing Sheets

METHOD AND APPARATUS FOR MEASURING DYNAMIC RESPONSE CHARACTERISTICS OF SHOCK ACCELEROMETER

BACKGROUND OF THE INVENTION

1. Field of the Invention

This invention relates to a method and an apparatus for measuring the dynamic response characteristics, including the gain characteristics and the phase characteristics, of a shock accelerometer of the type used for measurements in drop impact tests conducted on containers for transporting radioactive wastes, impact tests conducted on structures, vehicle collision tests and the like.

2. Prior Art Statement

Shock accelerometers are employed in such wide-ranging fields of industrial measurement as collision tests conducted on structures, drop impact tests, stress analysis tests and vibration analysis tests.

As a method for calibrating an shock accelerometer, there is known that set out in ISO 5347, which is a method using a combination of a vibrator and a laser interferometer. With this conventional method, however, it is difficult to carry out high-precision calibration because as the frequency of the vibrating table becomes higher, the vibration amplitude becomes smaller and the waveform deviates from sinusoidal. While high frequencies excitation is possible by using a resonant vibrating table, the excitation frequency that can be produced is determined by the particular vibrating table so that where it is desired to measure the characteristics of an accelerometer over a wide frequency range, it becomes necessary to use a large number of resonant vibrating tables with different excitation frequencies. This leads to unreliable calibration and is also uneconomical. Moreover, although the conventional calibration method is intended for use at vibration accelerations of 100 m/s$^2$ or less, it is in fact used for calibration at higher vibration accelerations because there is no other method available. The reliability of the detected values is thus highly doubtful.

Since an accelerometer can be modeled as an oscillating system consisting of a spring and a mass, it has its own resonant frequency. Because of this, the gain (sensitivity) of an accelerometer is a function of the frequency of the input acceleration. Generally, the gain is constant in the low frequency region but increases as the frequency of the input acceleration approaches the resonant frequency. As the accelerometer can be used only in the region of constant gain, the frequency at which the gain increases by a prescribed rate is defined as the upper limit frequency at which the accelerometer can be used. The relationship between the frequency of the input acceleration and the gain will be referred to here as the gain characteristics.

In any dynamic system, of which the accelerometer is only one example, the system delay increases as the timewise variation in the input signal becomes faster, causing a phase lag between the input signal and the output signal. Therefore, similarly to the case of the gain, the frequency at which the phase lag comes to exceed the tolerable limit is defined as the upper limit frequency for the phase.

Elastic waves and plastic waves are generated in the interior of an object to which an accelerometer is attached when the object is subjected to an impact. In the measurement of shock acceleration for evaluation of breaking, the acceleration output signal is sometimes passed through an electrical filter for removing the effect of the elastic waves. Where the phase of the filter output signal has to be taken into consideration, it is indispensable to have prior knowledge of the relationship between the phase lag and the frequency of the accelerometer output signal itself, that is to say, of the phase characteristics. Also, in cases where the signal output by the accelerometer is to be used as a trigger signal and the timing thereof is subject to severe conditions, it becomes impossible to use phase compensation and other such control techniques unless the phase characteristics are known.

Thus for calibrating an shock accelerometer it is necessary to determine both the gain characteristics and the phase characteristics.

OBJECT AND SUMMARY OF THE INVENTION

The object of this invention is to provide a method and an apparatus for measuring the dynamic response characteristics of an shock accelerometer and, specifically, to provide such a method and apparatus which enable accurate and easy measurement of the gain characteristics and the phase characteristics of an shock accelerometer.

For realizing this object this invention provides a method and apparatus for measuring the dynamic response characteristics of an shock accelerometer wherein the accelerator to be tested is fixed on one end surface of a rod supported to be axially moveable, a strain gage is provided on the rod slightly apart from the same end, the other end of the rod is imparted with an impact so as to produce an elastic wave that propagates through the interior of the rod and is reflected by the end surface to which the accelerometer is fixed, the acceleration at the time of this reflection is input to the accelerometer, an elastic wave required for ascertaining the acceleration input to the accelerometer is measured by the strain gage provided at a position apart from the end surface of the rod, the outputs of the accelerometer and the strain gage are Fourier transformed or Laplace transformed mathematically and the resulting values are subjected to a processing such as compensation for error.

Thus an elastic wave produced inside the rod generates a pulse-like acceleration at the instance of reflection and this acceleration input to the accelerometer is detected by the strain gage. The outputs of the strain gage and the accelerometer are then subjected to data processing to determine the dynamic response characteristics of the accelerometer. The results obtained are thus highly reliable and, by adjusting the magnitude of the impact imparted to the rod, it is possible to determine the characteristics of the accelerometer over a wide frequency range.

The above and other features of the present invention will become apparent from the following description made with reference to the drawings.

DETAILED DESCRIPTION OF THE PREFERRED EMBODIMENT

Figure 1:
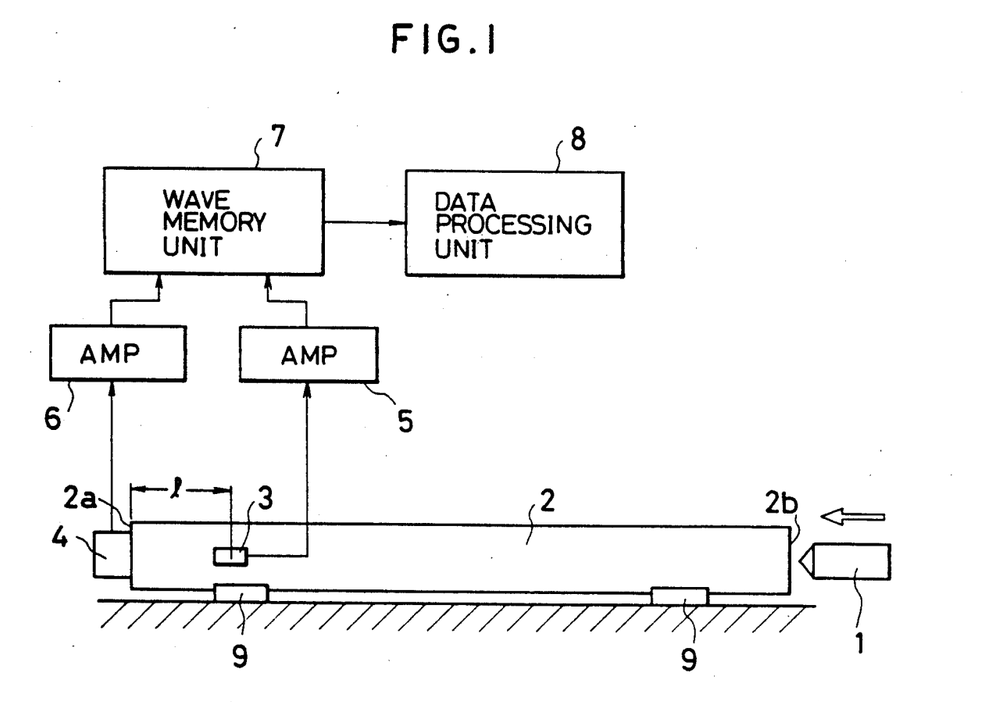
FIG. 1 is a schematic view of an apparatus for implementing the method for measuring the dynamic response characteristics of an shock accelerometer according to this invention.

FIG. 1 is a block diagram of one embodiment of the apparatus in accordance with the present invention for measuring the dynamic response characteristics of an shock accelerometer. The apparatus comprises a rod 2 rested on a table 9 so as to be free to move in its axial direction. An accelerometer 4 to be tested is attached to one end surface 2a of the rod 2 by means of a screw or the like (not shown). A semiconductor strain gage 3 with good response characteristics and low noise is provided on the rod 2 at a prescribed distance l from the end surface 2a to which the accelerometer 4 is attached. As the bottom of the accelerometer to which the rod 2 is attached is generally made of stainless steel or titanium, it is preferable for the rod 2 to be made of a steel, stainless steel or the like having an acoustic impedance equal to or larger than these materials. Where the rod used has a circular cross section, it is preferable to use one of a length that is 10 or more times the diameter since it is necessary for the ratio between the diameter and the length to be such that the propagated elastic wave can be considered to be a one-dimensional wave.

The strain gage 3 is provided at a position apart from the end surface 2a by the distance l so as to be capable of discriminating between the elastic wave (compression wave) propagating toward the end surface 2a of the rod 2 and the elastic wave (tensile wave) reflected from the end surface 2a.

Figure 2:
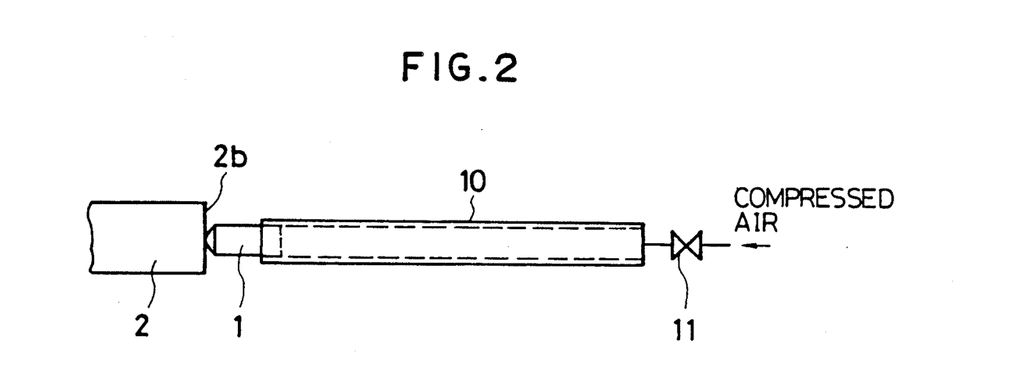
FIG. 2 is a schematic view of an apparatus for imparting an impact to a rod of the apparatus shown in FIG. 1.

Once the accelerometer 4 to be tested and the strain gage 3 have been fitted on the rod 2 in the aforesaid manner, an appropriate object 1 is caused to collide with the other end surface 2b of the rod 2 so as to impart an impact. This impact is for producing an elastic wave within the rod 2 and an example of how this is accomplished is illustrated in FIG. 2. A conically-pointed missile 1 is inserted into a launching tube 10 and compressed air is introduced into the launching tube 10 by opening a valve 11, accelerating the missile 1 and causing it to collide with the end surface 2b of the rod 2 which has been positioned in front of the muzzle of the launching tube 10, whereby an elastic wave is produced within the rod 2. This method is preferable since the collision velocity of the missile 1 can be easily measured with high accuracy using laser beams. Any of various other ways can be used for accelerating the missile 1 in place of that relying on compressed air described above. For example, it can be accelerated electromagnetically, by static electricity, by an explosive, by the force of the earth's gravity, or by energy stored in a elastic body. Insofar as it is possible to control the collision velocity without restriction and to generate an elastic wave in the rod 2, it is also possible to employ various other methods such as by producing the elastic wave within the rod 2 by striking the end surface 2b of the rod with a hammer, by attaching a piezoelectric element to the end surface 2b and producing a pulse-shaped resilient wave by applying a driving voltage to the piezoelectric element, by directing a powerful pulse laser beam onto the end surface 2b and producing a pulse-shaped resilient wave by the instantaneous thermal expansion of the rod 2, or by causing an shock wave produced in a gas by the explosion of an explosive or by a shock tube to impinge on the end surface 2b. The rod should not undergo plastic deformation at the time the impact is applied to the end surface thereof and adequate care must be taken in this regard. For example, when the impact is generated by the collision of a missile, plastic deformation of the rod is avoided by selecting a missile made of a material such as aluminum which is sufficiently softer than that of the rod selected.

The collision velocity at the end surface of the rod is appropriately selected in light of the characteristics of the shock accelerometer.

As explained in the foregoing, an elastic wave is produced in the interior of the rod 2 when an impact is applied to the end surface 2b thereof. This wave propagates toward the end surface 2a to which the accelerometer 4 is attached. At the time that the elastic wave reaches the end surface 2a and is reflected thereby, there is, as shown in Eq. (1), produced at the end surface 2a an acceleration a(t) equal to twice the product of the propagation velocity C of the elastic wave and the strain rate $\epsilon$ near the end surface. This acceleration a(t) is the input acceleration to the accelerometer 4 attached to the end surface 2a.

$$a(t) = 2C\epsilon \quad (1)$$

wherein a(t) is the acceleration at the end surface 2a to which the accelerometer 4 is attached.

Since the strain gage 3 is provided on the rod 2 at a distance $l$ from the end surface 2a, the relationship between the strain measured by the strain gage 3 and the acceleration a(t) at the end surface 2a is as given by Eq. (2).

$$a(t) = 2C\epsilon(t - l/C) \quad (2)$$

Therefore the acceleration a(t) calculated by Eq. (2) becomes the input signal to the accelerometer 4 attached to the end surface 2a.

Figure 3A:
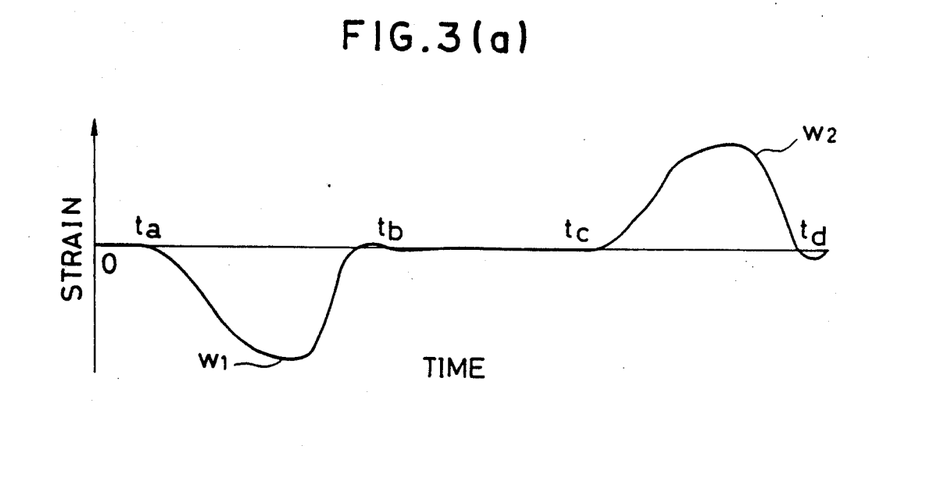
FIG. 3(a) is a graph showing the waveform of an elastic wave measured with a strain gage.
Figure 3B:
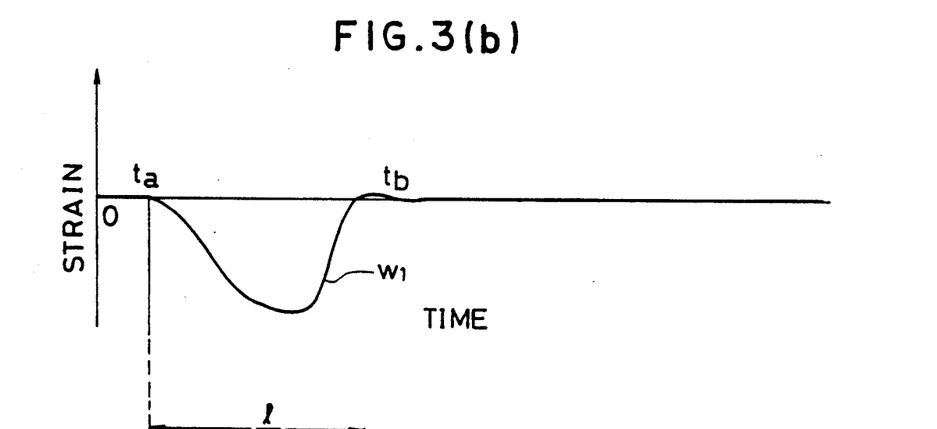
FIG. 3(b) is a graph showing the waveform of a strain wave used for calculating the acceleration which is the input signal of an accelerometer.
Figure 3C:
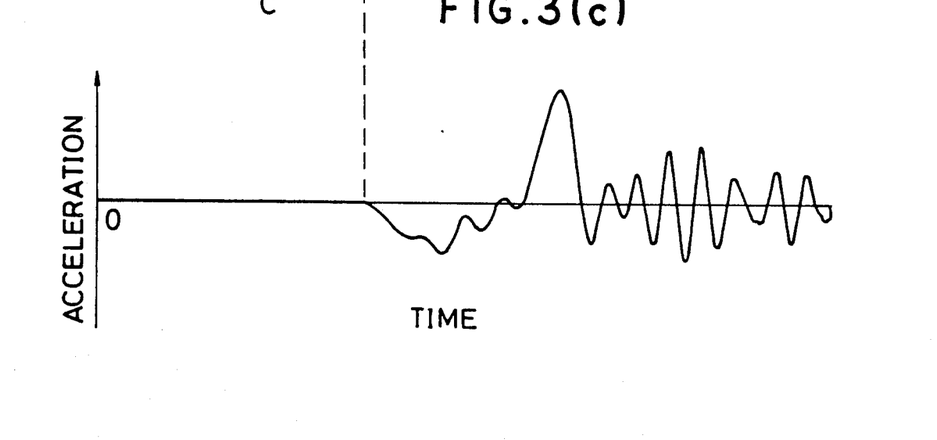
FIG. 3(c) is a graph showing an example of the waveform of the output signal of an accelerometer being tested.

As shown in FIG. 3(a), the waveform of the stress wave measured by the strain gage 3 first, between times $t_a$ and $t_b$, assumes the elastic waveform $W_1$ of a compression wave traveling toward the end surface 2a and then, between times $t_c$ and $t_d$, assumes the waveform $W_2$ of the elastic waveform of the tensile wave reflected back from the end surface 2a. The waveform between times $t_c$ and $t_d$ is that of the expansion stress wave produced by reflection from the end surface 2a and since it is traveling in the direction of the end surface 2b at which the impact occurred, it has no effect on the production of the input acceleration input to the accelerometer 4. The strain rate $\epsilon$ used when calculating in accordance with Eq. (2) the acceleration which is to become the input signal to the accelerometer 4 is derived from the strain signal ($\epsilon_m$) of the waveform $W_1$ of the compression wave appearing between times $t_a$ and $t_b$ in FIG. 3(b). An example of the output signal $a_m(t)$ produced by the accelerometer 4 upon receiving the aforesaid signal is shown in FIG. 3(c). This output signal is amplified by an amplifier 6, converted to a digital signal by a wave memory 7 which functions both as an A/D convertor and as a memory, stored in memory, and sent to a data processing unit 8. The output signal from the strain gage 3 is similarly amplified by an amplifier 5, converted to a digital signal and stored in memory in the wave memory 7, and sent to the data processing unit 8.

In the data processing unit 8, the output signal $a_m(t)$ from the accelerometer 4 and the signal $\epsilon_m$ from the strain gage, namely the signal corresponding to the compression wave after removal of the expansion stress wave from the output of the strain gage 3, are used to calculate the gain characteristics and the phase characteristics of the accelerometer in accordance with the Eq. (3) below.

The calculation of the gain characteristics and the phase characteristics of the accelerometer is in fact exactly the same as calculating what in control engineering is referred to as the transfer function $G(\omega)$. The transfer function is defined as the function obtained by dividing the Laplace transform of the output signal of a linear system by the Laplace transform of the input signal of the same system. Thus for obtaining the transfer function of an accelerometer it suffices to divide the Laplace transform of the accelerometer output signal produced when the accelerometer is imparted with a known acceleration by the Laplace transform of the input acceleration signal.

Specifically, where $a_m(t)$ is the acceleration signal appearing as the output of the accelerometer 4 and $G(\omega)$ is the transfer function of the accelerometer 4, we have $$L[a_m(t)] = G(w) \cdot L[2C\epsilon_m(t - l/C)] \quad (3)$$

where $\omega$ is the angular frequency and $L[\ ]$ is the Laplace transform operator. While the Eq. (3) is mathematically a Laplace transform, numerically it is the same as a fast Fourier transform. Moreover in view of the frequency bandwidth of the observation system and the like, a physically significant upper limit frequency is present in the Fourier transform. Signal components in the region above this upper limit frequency are removed. In other words, this is a filter calculation. Since in actuality the measured detection value is the strain as a physical quantity not the strain rate Eq. (3) can be rewritten using the nature of the Laplace transform in differentiation to obtain the transfer function G(w) of the accelerometer as $$G(\omega) = \frac{L[a_m(t)]}{j2\omega CL[\epsilon_r(t - l/C)]} \quad (4)$$

where j is an imaginary unit.

The gain characteristic g(w) of the accelerometer can be obtained from Eq. (4) as $$g(\omega) = |G(\omega)| \quad (5)$$

Since the strain gage 3 is disposed at the distance l from the end surface 2a, it is necessary to make a compensation taking account of the dispersivity. Defining the strain waveform at the free end surface 2a obtained by Skalak's analysis as $\epsilon_r(t)$ and the waveform actually measured by the strain gage under identical conditions to the Skalak's analysis as $\epsilon_g(t)$, the gain compensation coefficient $K(\omega)$ becomes $$K(\omega) = \left| \frac{L[\epsilon_g(t - l/C)]}{L[\epsilon_r(t)]} \right| \quad (6)$$

Therefore, the compensated gain characteristic $g_c(\omega)$ of the accelerometer becomes $$g_c(\omega) = K(\omega)g(\omega) \quad (7)$$

Since the phase characteristic of the accelerometer 4 is simply the relationship between the phase of the transfer function and the frequency, the phase characteristic $\phi(\omega)$ can be obtained from Eq. (4) as $$\phi(\omega)(=\arg[G(\omega)] \qquad (8)$$

while the phase compensation coefficient $K(\omega)'$ can be expressed as $$K(\omega)'=\arg\{L[\epsilon_g(t-\mathit{X}/C)]/L[\epsilon_t(t)]\} \qquad (9)$$

Therefore, the compensated phase characteristic $\phi_c(\omega)$ of the accelerometer becomes $$\phi_c(\omega)=\phi(\omega)+K(\omega)' \qquad (10)$$

Figure 4:
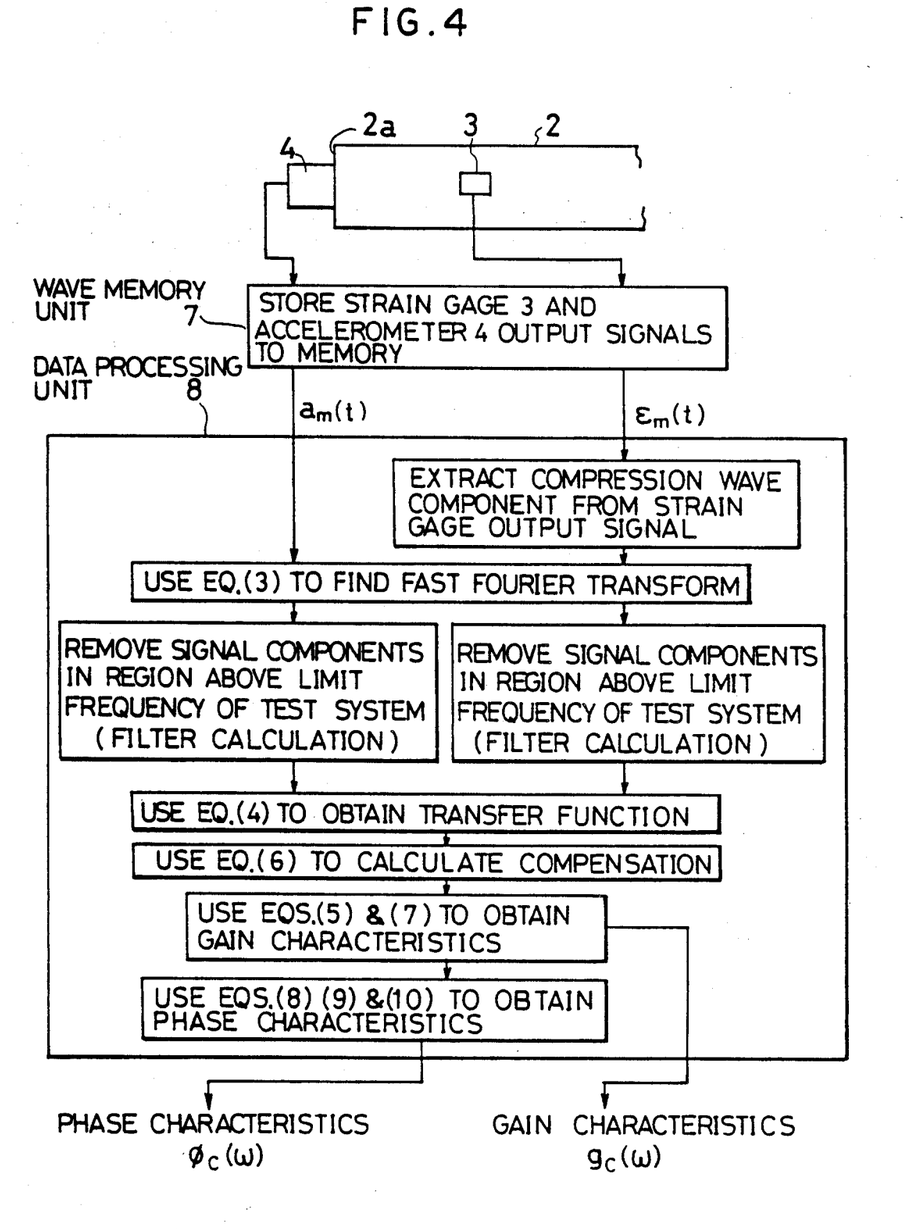
FIG. 4 is a flowchart showing the steps for obtaining the accelerometer gain and phase characteristics from the signals output by the accelerometer and a strain gage.

The calculation carried out in the data processing unit 8 based on the output signal of the accelerometer 4 and the output signal of the strain gage 3 can be expressed in the form of a flowchart as shown in FIG. 4. As the strain gage output signal received from the wave memory 7 includes a compression wave component and an expansion tensile wave component, only the compression wave component is extracted and used for further calculating the phase lag for the distance between the strain gage 3 and the end surface 2a. On the other hand, the Fourier transform component is, if necessary, extracted from the output signal of the accelerometer 4 and the two signals Fourier-transformed according to Eq. (3), whereafter the signal components thereof in the region exceeding the limit frequency based on the frequency bandwidth and dynamic range of the amplifier and the wave memory unit are removed.

The so-processed signal is then used for calculating the transfer function according to Eq. (4), whereafter the gain characteristic is calculated according to Eqs. (5), (6) and (7) and the phase characteristic is calculated according to Eqs. (8), (9) and (10).

From the gain characteristic and the phase characteristic obtained in the foregoing manner it is possible to determine the upper limit frequency and the resonant frequency of tested accelerometer and thus to determine the range within which the accelerometer is of use and reliable.

Specific examples of the invention will now be described.

A stainless steel (SUS 304) rod of circular cross section and measuring 30 mm in diameter and 2000 mm in length was supported on four bearing steel balls so as to be movable in its axial direction. A B&K Model 4393 shock accelerometer manufactured by Brüel & Kjaer selected as the shock accelerometer to be tested was attached to one end surface of the rod with M3 screws tightened to a torque of 1.1 N/m and two strain gages (Model KSK-2-E4-11 manufactured by Kyowa Dengyo of Japan and having an electrical resistance of 122 Ω) measuring 2 mm in length were attached to the rod in face-to-face relation at a position 625 mm apart from the same end surface.

A stainless steel launching tube measuring 14.8 mm in inside diameter and 1500 mm in length was disposed opposite the other end surface of the rod in the manner shown in FIG. 2. A cylindrical projectile made of pure aluminum measuring 14.6 mm in diameter and 100 mm in length and having a conical tip with an included angle of 150° was placed in the launching and tube propelled by compressed air to collide with the rear end surface of the rod. The collision velocity of the projectile was 10.0 m/sec as derived from the measured time required for the projectile to pass between two laser beams.

The elastic wave produced in the rod was detected by the strain gage and the detection signal was sent via a bridge circuit and a DC amplifier to a wave memory unit for storage. The output of the accelerometer fixed on the rod was forwarded via a charge amplifier to the wave memory unit for storage.

Figure 5:
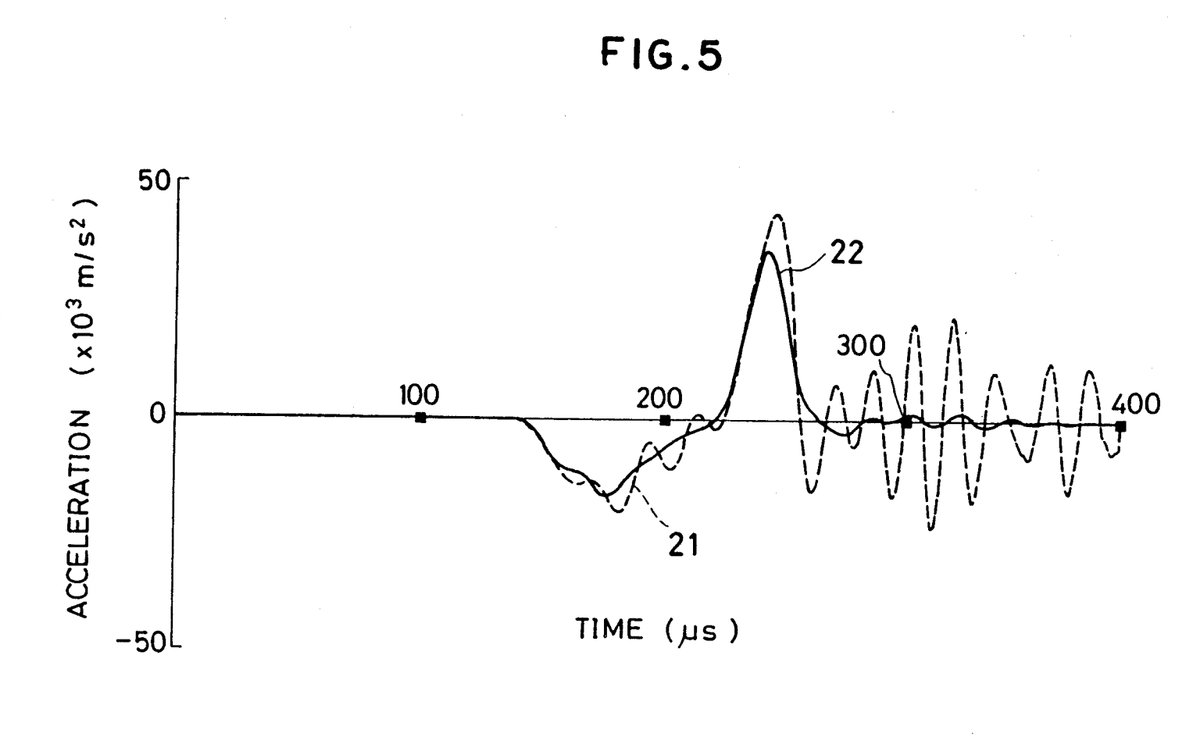
FIG. 5 is a graph showing the acceleration of the end surface of a rod calculated from the output of a strain gage together with the output of an accelerometer (B&K Model 4393).

The graph of FIG. 5 shows the wave output by the accelerometer in the foregoing experiment (curve 21) and the time course change in the acceleration of the end surface 2a calculated from the output of the strain gage according to Eq. (2) (curve 22). While the output of the accelerometer exhibits ringing thought to be due to resonance, aside from this ringing its behavior agrees well with the calculated acceleration. From this, it can be assumed that Eq. 2 is substantially valid.

Figure 6A:
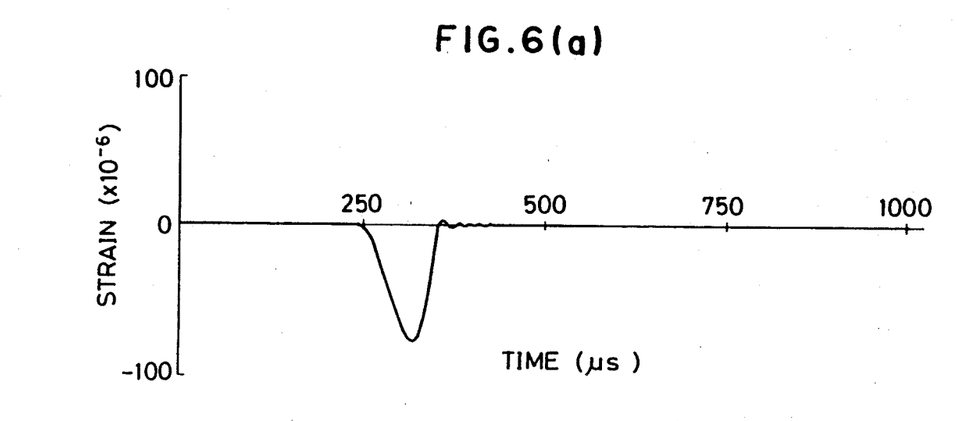
FIG. 6(a) is a graph showing an incident pulse observed by a strain gage in accordance with the method of the present invention.
Figure 6B:
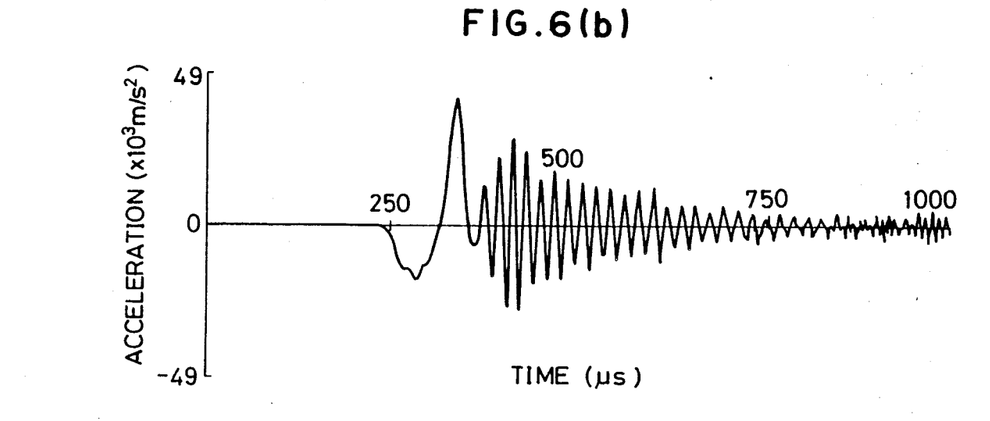
FIG. 6(b) is a graph showing the output waveform of a accelerometer being tested determined by the method of the present invention.

FIG. 6($a$) shows the incident pulse measured by the strain gage and FIG. 6($b$) shows the signal output by the accelerometer at the end surface. From FIG. 6($a$) it can be seen that the duration of the incident pulse was about 113 μs and that the peak strain was $-77\times 10^6$. From FIG. 6($b$) it can be seen that the signal output by the accelerometer exhibited a positive peak acceleration of $+4.1\times 10^4$ m/s$^2$ and a negative peak acceleration of $-1.8\times 10^4$ m/s$^2$.

Figure 7A:
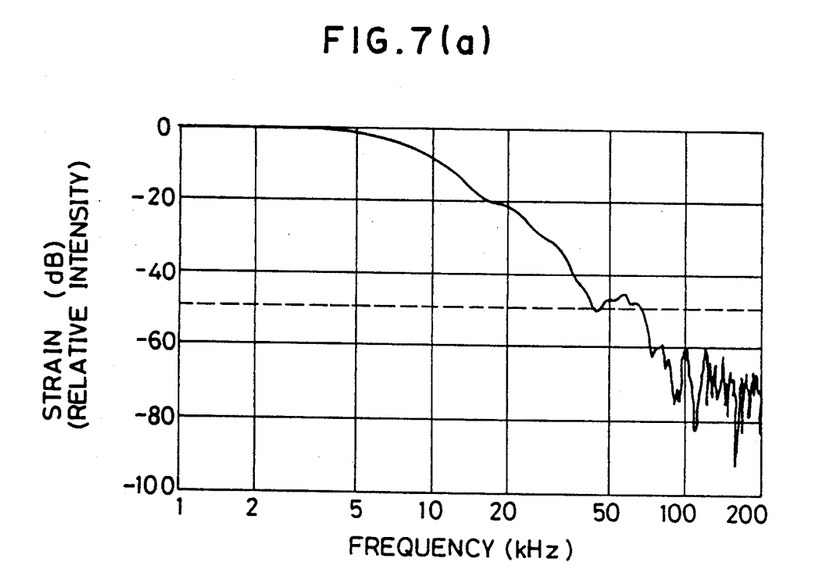
FIG. 7(a) is a graph showing the spectrum of the signal waveform of FIG. 6(a).
Figure 7B:
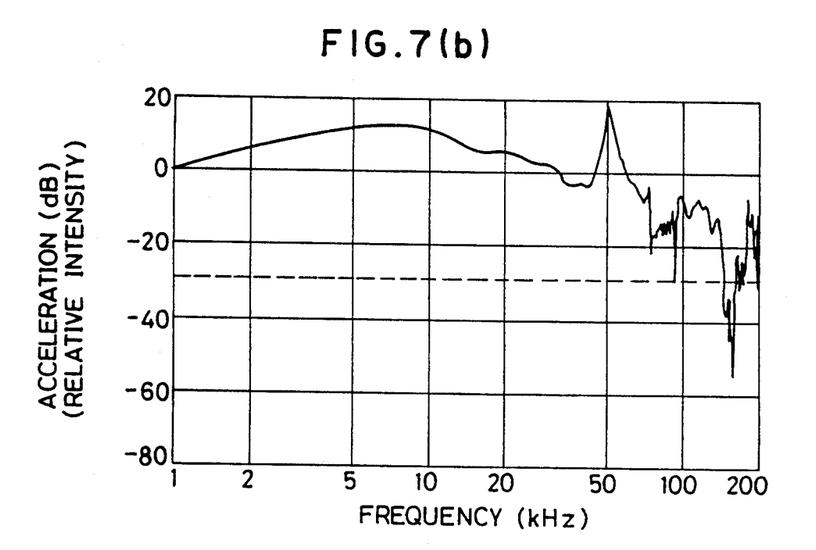
FIG. 7(b) is a graph showing the spectrum of the signal waveform of FIG. 6(b).

FIGS. 7($a$) and ($b$) show the spectra of the signals shown in FIGS. 6($a$) and 6($b$), respectively. The broken lines indicate the dynamic range limit determined by the resolution of the 8-bit A/D converter in the wave memory unit. More specifically, signals stored in the wave memory unit in the frequency range with spectra above these broken lines have physical significance.

The results of this experiment are thus that, as shown in FIG. 7($a$), the strain gage signal is valid between 1 kHz-70 kHz and that, as shown in FIG. 7($b$), the acceleration signal is valid between 1 kHz-147 kHz.

Figure 8A:
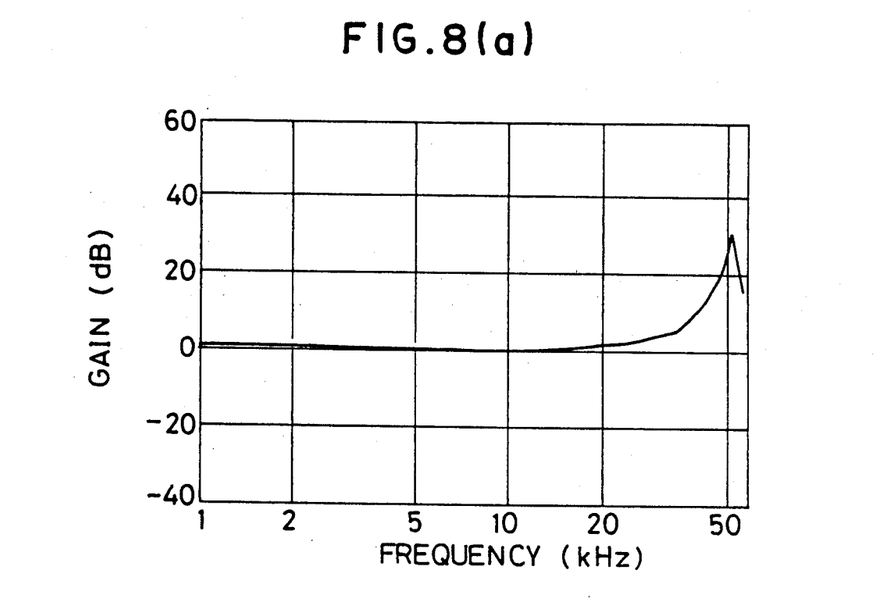
FIG. 8(a) is a graph showing the gain characteristics of an accelerometer determined by the method of the present invention from the signals shown in FIGS. 6(a) and (b).
Figure 8B:
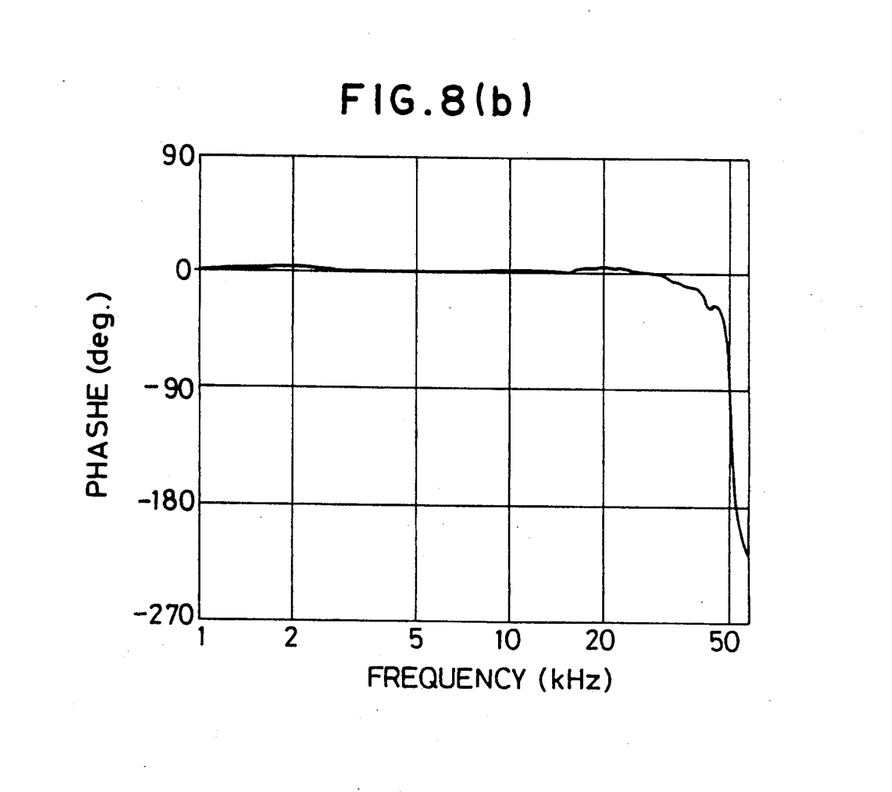
FIG. 8(b) is a graph showing the phase characteristics of an accelerometer determined by the method of the present invention from the signals shown in FIGS. 5(a) and (b).

FIG. 8($a$) shows the gain characteristics of accelerometer after compensation for the dispersivity of the elastic wave based on the compensation coefficient of Eq. (6). FIG. 8($b$) shows the compensated phase characteristics of the accelerometer.

It can be seen from FIG. 8($a$) that the resonant frequency of the tested B&K Model 4393 shock accelerometer was 52 kHz, that the upper limit frequency below which the shock accelerometer could be used was, in terms of gain, 16 kHz, and, in terms of phase, 33 kHz. The manufacturer's data gave a mounted resonant frequency of 55 kHz and an upper limit response frequency of 17 kHz.

The gain and phase characteristics of a B&K Model 8309, an Endevco Model 2271A, an Endevco Model 2270, a Kistler Model 8005 and a Columbia Model 383 were tested using the same apparatus as in the experiment described above except that the projectile was changed for each test.

Figure 9A:
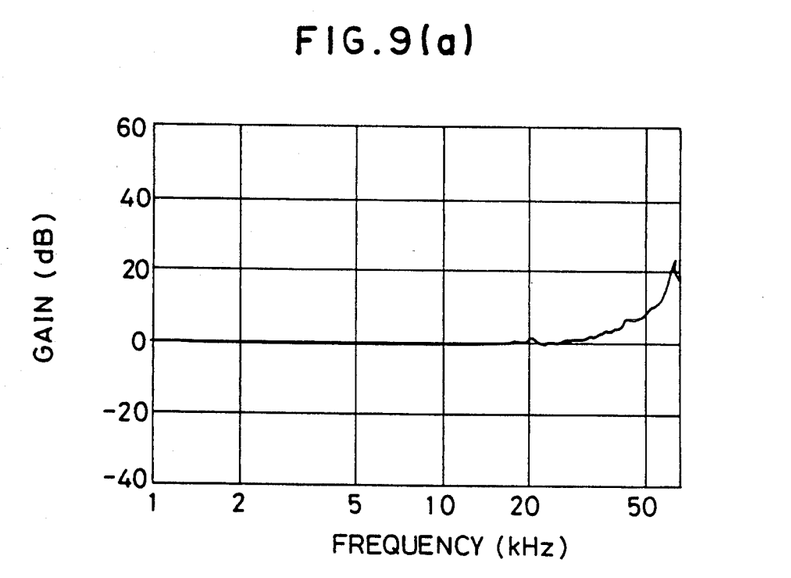
FIG. 9(a) is a graph showing the gain characteristics of a B&K Model 8309 accelerometer determined by the method of the present invention and FIG. 9(b) is a graph showing the phase characteristics of the same accelerometer determined by the method of the present invention.
Figure 9B:
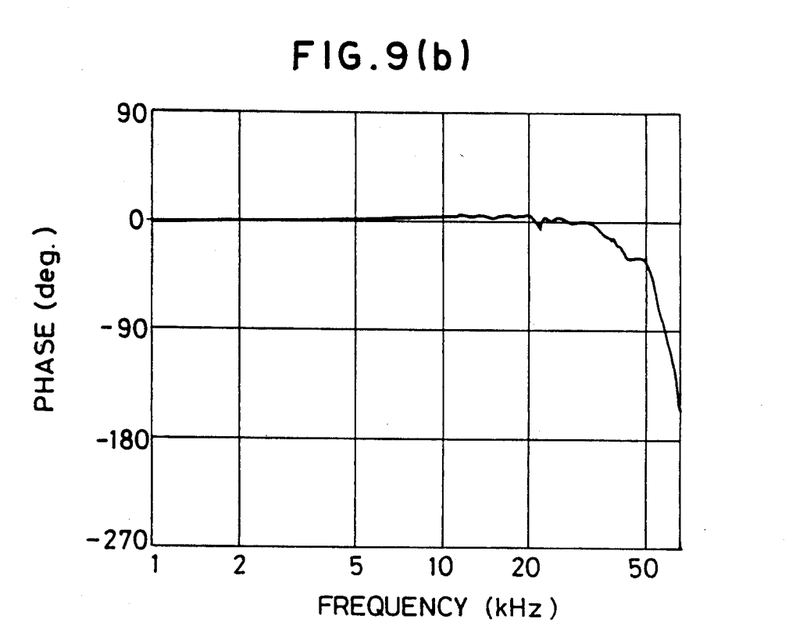
Figure 10A:
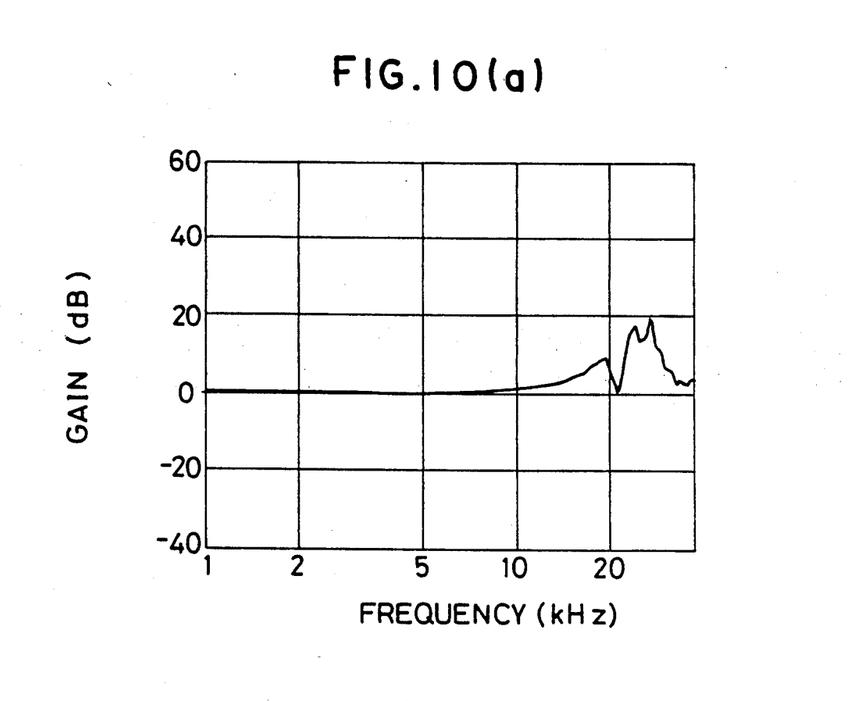
FIG. 10(a) is a graph showing the gain characteristics of an Endevco Model 2271A accelerometer determined by the method of the present invention and FIG. 10(b) is a graph showing the phase characteristics of the same accelerometer determined by the method of the present invention.
Figure 10B:
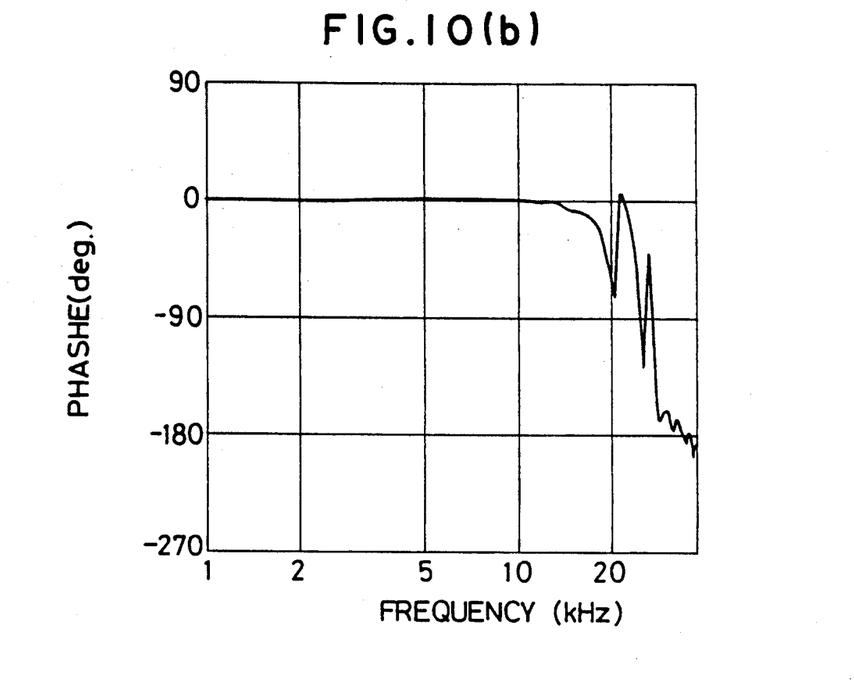
Figure 11A:
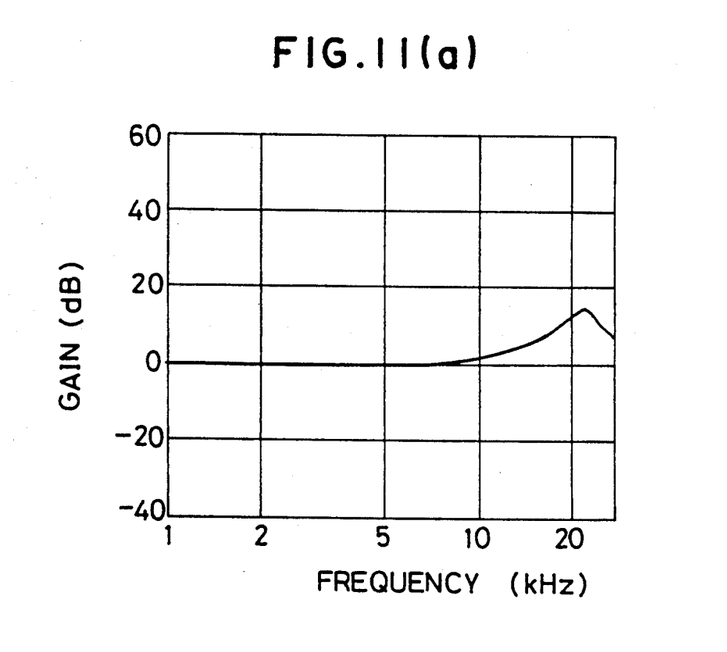
FIG. 11(a) is a graph showing the gain characteristics of an Endevco Model 2270 accelerometer determined by the method of the present invention and FIG. 11(b) is a graph showing the phase characteristics of the same accelerometer determined by the method of the present invention.
Figure 11B:
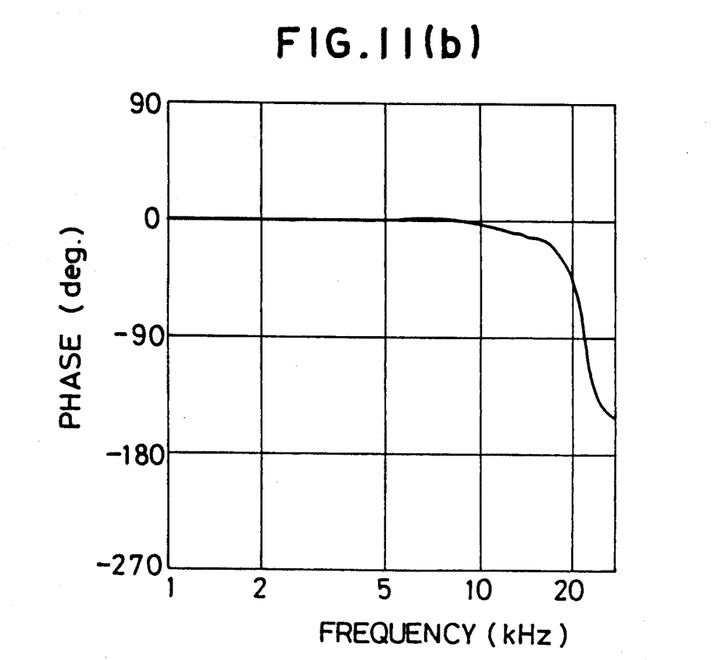

The type of screw used for mounting each accelerometer on the end surface of the rod, the screw torque, the collision velocity of the projectile, the incident pulse and the peak acceleration are shown in Table 1, while the mounted resonant frequency and the upper limit response frequency found for each accelerometer is shown in Table 2 together with corresponding manufacturer's data. The gain characteristics and phase characteristics found for the B&K Model 8309 are shown in FIGS. 9($a$) and 9($b$), those found for the Endevco Model 2271A are shown in FIGS. 10($a$) and ($b$), those found for the Endevco Model 2270 are shown in FIGS.

Figure 12A:
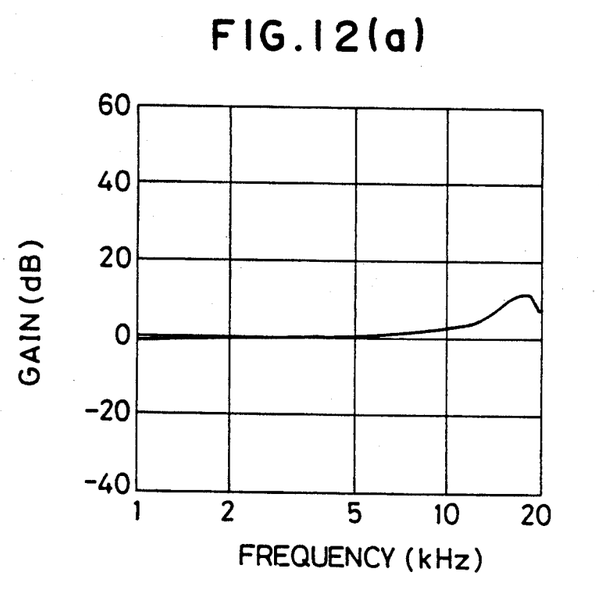
FIG. 12(a) is a graph showing the gain characteristics of a Kistler Model 8005 accelerometer determined by the method of the present invention and FIG. 12(b) is a graph showing the phase characteristics of the same accelerometer determined by the method of the present invention.
Figure 12B:
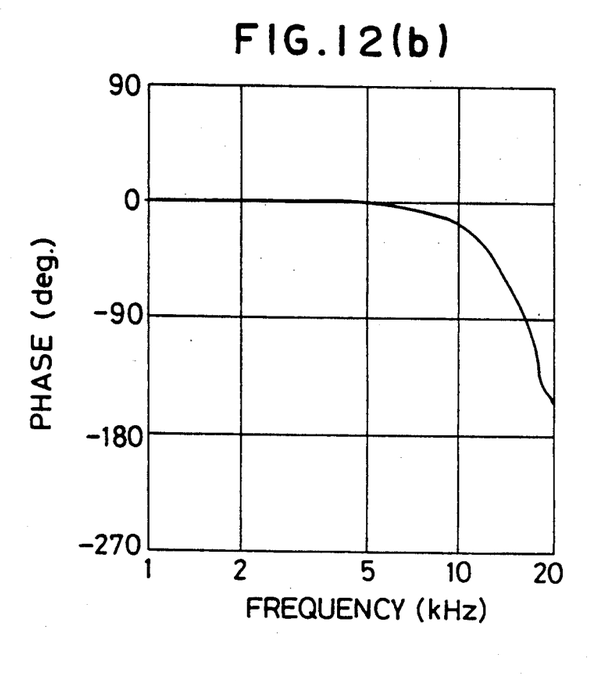
Figure 13A:
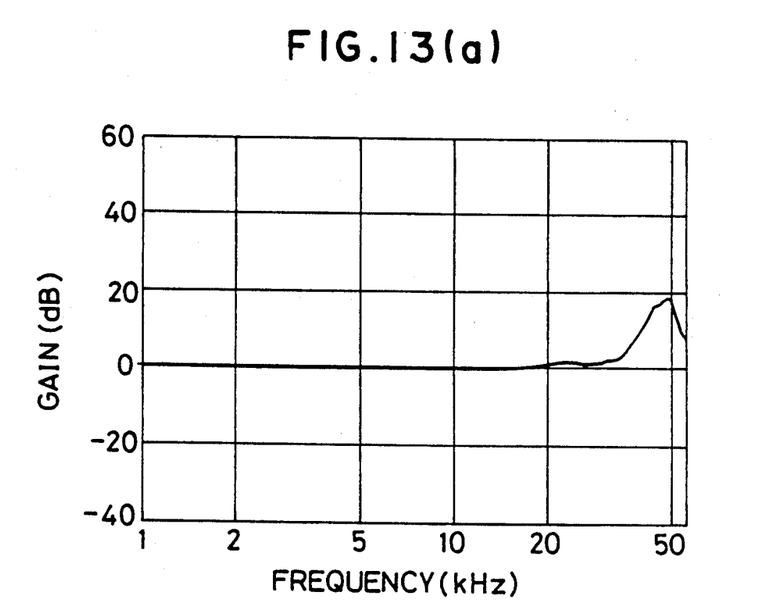
FIG. 13(a) is a graph showing the gain characteristics of a Columbia Model 383 accelerometer determined by the method of the present invention and FIG. 13(b) is a graph showing the phase characteristics of the same accelerometer determined by the method of the present invention.
Figure 13B:
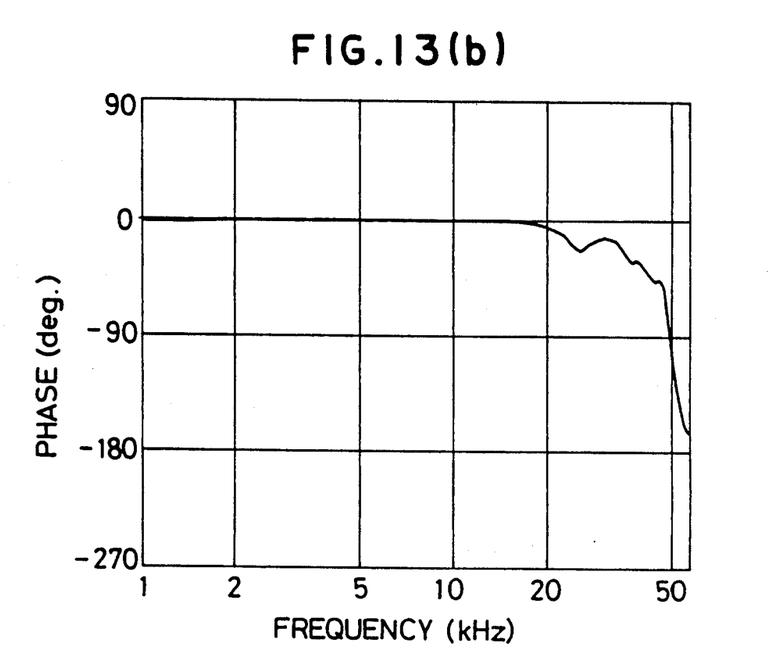

11(a) and 11(b), those found for the Kistler Model 8005 are shown in FIGS. 12(a) and 12(b), and those found for the Columbia Model 383 are shown in FIGS. 13(a) and 13(b).

TABLE 1

| Accelerometer | Mounting Stud | Mounting Torque | Speed of Collision | Incident Pulse Duration | Incident Pulse Peak Strain | Peak Acceleration (Output from Accelerometer) |
|---|---|---|---|---|---|---|
| B & K 8309 | M5 | 1.1 Nm | 9.4 m/s | 119 μs | $-72 \times 10^{-6}$ | $+3.3 \times 10^4$ m/s$^2$ / $-1.4 \times 10^4$ m/s$^2$ |
| Endevco 2271A | 10-32 UNF | 2.3 Nm | 9.8 m/s | 117 μs | $-75 \times 10^{-6}$ | $+4.2 \times 10^4$ m/s$^2$ / $-1.6 \times 10^4$ m/s$^2$ |
| Endevco 2270 | ¼-28 | 2.3 Nm | 8.7 m/s | 121 μs | $-63 \times 10^{-6}$ | $+3.8 \times 10^4$ m/s$^2$ / $-1.5 \times 10^4$ m/s$^2$ |
| Kistler 8005 | M8 | 2.3 Nm | 8.8 m/s | 115 μs | $-69 \times 10^{-6}$ | $+2.9 \times 10^4$ m/s$^2$ / $-1.5 \times 10^4$ m/s$^2$ |
| Columbia 383 | 10.32 UNF | 1.7 Nm | 9.4 m/s | 115 μs | $-70 \times 10^{-6}$ | $+4.7 \times 10^4$ m/s$^2$ / $-1.9 \times 10^4$ m/s$^2$ |

TABLE 2

| Accelerometer | Mounted Resonant Frequency Test Results by Invention | Mounted Resonant Frequency Manufacturer's Data | Response Frequency (Upper Limit) Test Results by Invention Gain (+1 dB) | Response Frequency (Upper Limit) Test Results by Invention Phase (−0.1 rad) | Response Frequency (Upper Limit) Manufacturer's Data |
|---|---|---|---|---|---|
| B & K 8309 | 63 kHz | 180 kHz | 27 kHz | 34 kHz | 54 kHz |
| Endevco 2271A | 19 kHz | 27 kHz | 10 kHz | 14 kHz | 4 kHz |
| Endevco 2270 | 22 kHz | >50 kHz | 10 kHz | 12 kHz | 10 kHz |
| Kistler 8005 | 18 kHz | 22 kHz | 7 Hz | 7 kHz | 4 kHz |
| Columbia 383 | 49 kHz | 80 kHz | 15 Hz | 20 kHz | 15 kHz |

In Table 1, the upper limit frequency below which the accelerometer can be used was judged from the gain as that below which the gain increased by 1 dB with increasing frequency and was judged from the phase as that at which the phase of the accelerometer response lagged by 0.1 rad.

As will be understood from the foregoing description, this invention enables the dynamic response characteristics of an shock accelerometer to be measured using an elastic wave and makes it possible to easily and reliably measure the dynamic response characteristics of accelerometers in acceleration ranges in which no standards have been established heretofore. It thus makes a major contribution to accelerometer calibration.

What is claimed is:

1. A method for measuring the dynamic response characteristics of an shock accelerometer comprising the steps of fixing a shock accelerometer whose dynamic response characteristics are to be measured to a first end surface of a rod, providing a strain gage on the rod at a prescribed distance from the first end surface for enabling independent detection of an incident elastic wave and a reflected elastic wave, imparting an impact to a second end surface of the rod thereby causing an elastic wave to propagate therethrough, inputting to the accelerometer as an acceleration signal an acceleration arising when the elastic wave propagates through the rod and is reflected by the first end surface, measuring the acceleration signal input to the accelerometer with the strain gage provided at a position apart from the first end surface, and calculating a gain characteristic and a phase characteristic of the accelerometer from a signal output by the accelerometer and a signal output by the strain gage.

2. A method for measuring dynamic response characteristics according to claim 1 wherein the gain characteristic and the phase characteristic are calculated by data processing including Fourier transformation of the signals output by the accelerometer and the strain gage.

3. A method for measuring dynamic response characteristics according to claim 2 wherein the values obtained by Fourier transformation are compensated for the dispersivity of the elastic wave based on Skalak's analysis.

4. A method for measuring dynamic response characteristics according to claim 1 wherein a compression wave component signal is extracted from the signal output by the strain gage.

5. A method for measuring dynamic response characteristics according to claim 1 wherein the elastic wave is produced by causing a projectile to collide with the second end surface of the rod.

6. An apparatus for measuring the dynamic response characteristics of shock accelerometer comprising a metal rod disposed to be movable in its axial direction, means provided on a first end surface of said metal rod for attaching to said first end surface a shock accelerometer whose dynamic response characteristics are to be measured on the basis of an acceleration signal input received by said shock accelerometer at said first end surface; a strain gage provided on the rod at a position apart from the first end surface for measuring the acceleration signal input to the shock accelerometer, means for imparting an impact to a second end surface of the rod for producing an elastic wave therein, and data processing means for calculating a gain characteristic and a phase characteristic from a signal output by the shock accelerometer and a signal output by the strain gage as a result of the elastic wave.

7. An apparatus according to claim 6 wherein the rod is of circular cross section and has a length at least ten times as great as its diameter.

8. An apparatus according to claim 6 wherein the metal rod is made of steel or stainless steel.

9. An apparatus according to claim 6 wherein the strain gage is disposed at a position at which an incident elastic wave and a reflected elastic wave can be independently detected when the elastic wave propagates to and is reflected by the first end surface.

10. An apparatus according to claim 6 wherein the means for imparting an impact to a second end surface comprises a launching tube, a projectile and a means for propelling the projectile.

* * * * *